(12) United States Patent
Humphreys

(10) Patent No.: US 8,709,039 B2
(45) Date of Patent: Apr. 29, 2014

(54) HEMOSTATIC DEVICES AND METHODS FOR USE THEREOF

(75) Inventor: Mitchell Humphreys, Cave Creek, AZ (US)

(73) Assignee: Humparkull, LLC, Cave Creek, AZ (US)

( * ) Notice: Subject to any disclaimer, the term of this patent is extended or adjusted under 35 U.S.C. 154(b) by 561 days.

(21) Appl. No.: 12/464,583

(22) Filed: May 12, 2009

(65) Prior Publication Data

US 2009/0281507 A1 Nov. 12, 2009

Related U.S. Application Data

(60) Provisional application No. 61/052,537, filed on May 12, 2008.

(51) Int. Cl.
- *A61B 17/08* (2006.01)
- *A61F 11/00* (2006.01)
- *A61M 5/00* (2006.01)

(52) U.S. Cl.
USPC .............................. 606/213; 606/108; 604/264

(58) Field of Classification Search
USPC ......... 606/111, 151, 154, 155, 195, 213, 215, 606/180, 108; 604/266, 269, 506, 164.05, 604/264
See application file for complete search history.

(56) References Cited

U.S. PATENT DOCUMENTS

| | | | | |
|---|---|---|---|---|
| 4,781,690 A | * | 11/1988 | Ishida et al. | 604/164.05 |
| 5,320,639 A | | 6/1994 | Rudnick | |
| 5,437,631 A | * | 8/1995 | Janzen | 604/506 |
| 5,514,158 A | * | 5/1996 | Kanesaka | 606/213 |
| 7,846,171 B2 | * | 12/2010 | Kullas et al. | 606/151 |
| 8,201,563 B2 | * | 6/2012 | Conquergood et al. | 606/180 |

OTHER PUBLICATIONS

Leung, Lawrence L.K., M.D.; Overview of Hemostasis. p. 1-18; 2013.

* cited by examiner

*Primary Examiner* — Julian W Woo
(74) *Attorney, Agent, or Firm* — Banner & Witcoff, Ltd.

(57) ABSTRACT

Materials and Methods for reducing or preventing bleeding and associated side effects during and after percutaneous medical procedures.

3 Claims, 4 Drawing Sheets

HEMOSTATIC DEVICES AND METHODS FOR USE THEREOF

TECHNICAL FIELD

This document relates to devices and methods for hemostasis during percutaneous medical procedures.

BACKGROUND

Percutaneous renal procedures can be used for a variety of medical purposes, including removal of kidney stones that are too large or too complex to be removed by another method, to remove or treat urothelial cancer in the urinary collecting system, or to treat kidney obstruction. These percutaneous surgical techniques generally utilize radiographic imagining to determine the precise location for desired access to a kidney. Using a needle, a puncture is made through the back and underlying tissues into the kidney. Once the tract has been established, a "safety" wire typically is passed from outside the body, through the kidney, and down the ureter toward the bladder. The tract is then dilated with a balloon or a rigid dilator, and a percutaneous sheath is placed over the dilating device. The sheath provides a portal through which different instruments and scopes can be placed in order to complete the percutaneous renal procedure.

SUMMARY

As many as a third of patients who undergo a percutaneous renal procedure will require a blood transfusion due to bleeding from the puncture of the kidney. Such bleeding can cause severe complications, including loss of renal function, pain, prolonged hospitalization, need for selective arterial embolization, or even the need for surgical removal of the kidney. This document provides hemostatic devices and methods for their use, which can reduce or prevent bleeding in percutaneous renal procedures and thus can reduce the risk of subsequent side effects. The devices provided herein can be readily deployed with minimal risk to the patient, and can be used for any suitable percutaneous procedure, including treatment of kidney stones, kidney biopsy, management of upper urinary tract cancers, or drainage of the kidney through a subject's back.

In one aspect, this document features an article comprising an elongate member having an exterior surface, a hemostatic material in contact with at least a portion of the exterior surface, and a covering that surrounds the hemostatic material and is adapted to move slidably over the elongate member. The elongate member can comprise a first end and a second end. The hemostatic material can be in contact with a portion of the external surface adjacent to the first end, and can extend over the hemostatic material from the first end toward the second end. The covering can extend to the second end, and can comprise a protrusion adjacent to the second end. The elongate member can have an interior lumen extending from the first end to the second end. The article can have a diameter of 20 to 26 French and a length from about 3 cm to about 20 cm. The elongate member can comprise a first portion having a first diameter and a second portion having a second diameter. The first diameter can be less than the second diameter, and the hemostatic material can be coated on the first portion.

In another aspect, this document features a kit comprising an article and a driver as described herein.

In another aspect, this document features a method for reducing bleeding in a subject during or after a medical procedure that includes utilizing a percutaneous sheath to gain access to an internal organ, the method comprising inserting an article as described herein into the subject through the percutaneous sheath, and actuating the article such that the tissue of the subject is contacted by the hemostatic material. The internal organ can be a kidney.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims

DESCRIPTION OF DRAWINGS

Like reference symbols in the various drawings indicate like elements.

DETAILED DESCRIPTION

Figure 1:
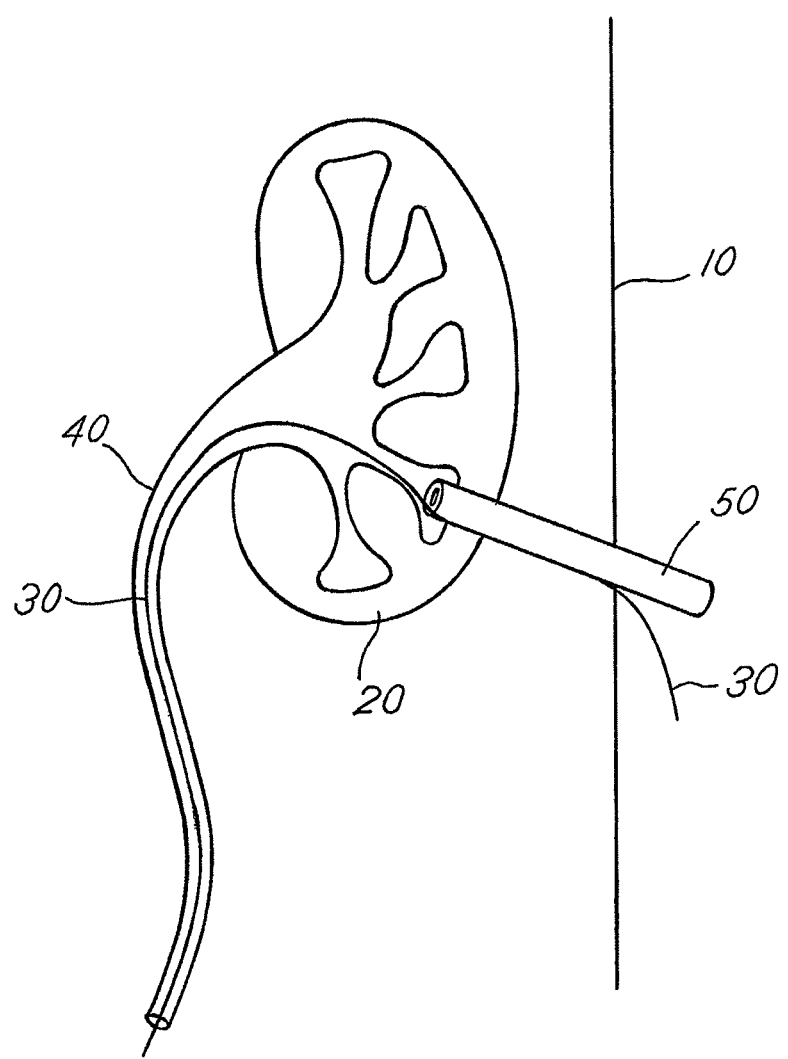
FIG. 1 is a depiction of a typical percutaneous renal procedure.

This document provides hemostatic devices and methods for their use in percutaneous procedures (e.g., percutaneous renal procedures). A typical percutaneous renal procedure is depicted in FIG. 1. A puncture is made through skin 10 of a subject's back, through the underlying tissues, and into kidney 20. Once a tract has been established, one or more wires (e.g., wire 30) can be passed through the tract, through the kidney, and down ureter 40 toward the bladder. When two wires are present, for example, a dilating device can be placed over one of the wires (the "working wire"), while the other wire (the "safety wire") can be along the outside of the dilating device. The tract then can be dilated, and percutaneous sheath 50 can be placed over the dilating device. Either the working wire or the safety wire can serve as a guide in case sheath 50 becomes displaced during a subsequent procedure. The size of sheath 50 can vary depending on the specific procedure, but often is 30 French (10.0 mm) in diameter. Sheath 50 can be hollow, providing a portal through which different instruments and scopes can be placed into the patient. Upon completion of a procedure, sheath 50 can be withdrawn from the subject, whereupon bleeding may occur from the kidney as well as the soft tissue and muscle of the back along the insertion/removal tract. The hemostatic devices described herein can be used to reduce or prevent such bleeding, as well as the associated side effects.

Figure 2:
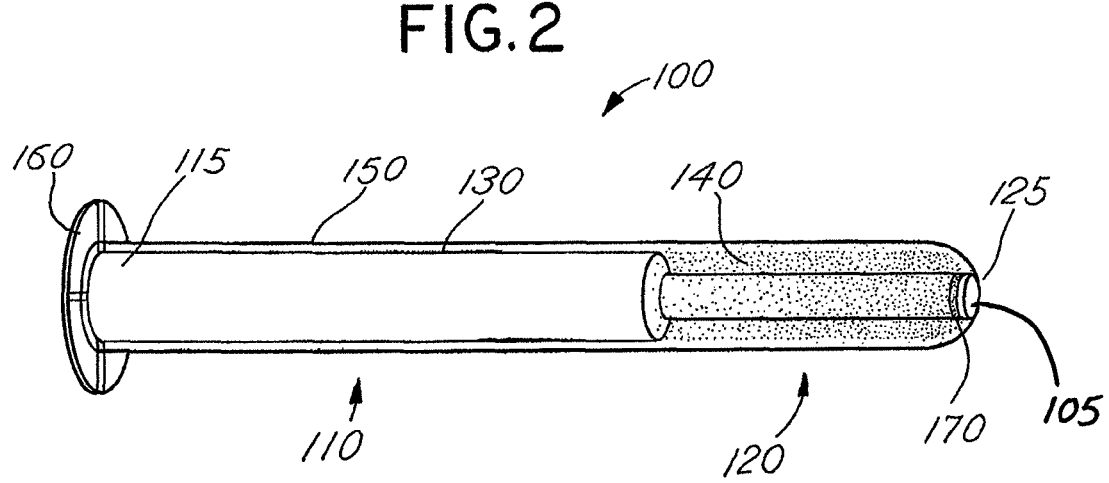
FIG. 2 is a side view of an embodiment of a hemostatic device.

FIG. 2 provides a depiction of a hemostatic device according to some embodiments provided herein. Device 100 can comprise cylinder 105 having proximal portion 110, proximal end 115, distal portion 120, distal end 125, and exterior surface 130. In some embodiments, cylinder 105 can be hollow such that it has an interior lumen extending through its length. This can allow for passage of, for example, wires, nephrostomy tubes, scopes, or any other suitable articles through device 100.

Device 100 can have any suitable size, and can be configured to move slidably within a percutaneous sheath. The most commonly used percutaneous sheaths have diameters of 24, 28, and 30 French (8.0, 9.3, and 10.0 mm, respectively). The devices provided herein can be 4 to 8 French less in diameter than the percutaneous sheath (e.g., 16, 18, 20, 22, 24, or 26 French). Further, device 100 can have any suitable length. For example, cylinder 105 can have a length from about 8 cm to about 22 cm (e.g., about 8 cm, about 9 cm, about 10 cm, about 11 cm, about 12 cm, about 13 cm, about 14 cm, about 15 cm, about 16 cm, about 17 cm, about 18 cm, about 19 cm, about 20 cm, about 21 cm; or about 22 cm). In addition, the devices can be made from any suitable material, including, for example, plastic.

Device 100 can have hemostatic material 140 coated on all or a portion of exterior surface 130 of cylinder 105. Hemostatic material 140 can accelerate a subject's natural ability to form blood clots. Any suitable hemostatic material can be used, including, without limitation, anti-fibrinolytics, fibrin sealants, matrix hemostats, and topical hemostatic agents. Particular examples of hemostatic materials include, without limitation, gelatins such as SURG1FOAM™ (Johnson & Johnson; Piscataway, N.J.) and GELFOAM® (Pharmacia & Upjohn Co.; New York, N.Y.); collagen materials such as AVITENE® and ULTRAFOAM™ (CR. Bard, Inc.; Murray Hill, N.J.); oxidized regenerated cellulose materials such as SURGICEL® Fibrillar and NU-KNIT™ (Johnson & Johnson); thrombin (e.g., pooled human or bovine thrombin); fibrin sealants such as TISSEEL® (Baxter Healthcare Corp.; Westlake Village, Calif.), EVICEL™ (Johnson & Johnson), VITAGEL™ (Orthovita, Inc.; Malvern, Pa.), and HEMASEEL® (Haemacure Corp.; Montreal, Quebec); polyethylene glycol polymers such as COSEAL® (Baxter Healthcare) and DURASEAL® (Confluent Surgical; Waltham, Mass.); albumin and glutaraldehyde compositions such as B1OGLUE® (Cryolife Inc.; Kennesaw, Ga.) and FOCALSEAL® (Focal, Inc.; Lexington, Mass.); glutaraldehyde resorcinol formalin and collagen (GRF; C.R. Bard, Inc.); gelatin and thrombin compositions such as FLOSEAL® (Baxter Healthcare Corp.) and SURGIFLO® (Johnson 8,z Johnson); granular zeolite powders such as QUIKCLOT® (Z-Medica Corp.; Wallingford, Conn.); chitin compositions such as HEMCON® (HemCon Medical Technologies, Inc.; Portland, Oreg.); and microporous polysaccharide hemospheres such as MPH® (Medafor Inc., Minneapolis, Minn.). Hemostatic material 140 can be dissolvable in urine and can be quickly reabsorbed to prevent clots or plugs in the urinary tract, fistulas (abnormal connections between the urinary collecting system and the retroperitoneum or back), or other problems.

The entirety of exterior surface 130 can be coated with hemostatic material 140, or just a portion (e.g., distal portion 120) can be coated with hemostatic material 140. In some embodiments, the diameter of cylinder 105 can vary along its length, such that it can have a smaller diameter in some areas than in others. Regions of smaller diameter can serve as reservoirs or channels for a hemostatic material. As depicted in FIG. 2, for example, the diameter of distal portion 120 can be reduced as compared to the diameter of proximal portion 110, and hemostatic material 140 can be placed over distal portion 120. In some cases, for example, outer surface 130 of cylinder 105 can define one or more channels (e.g., channels extending from distal end 125 along distal portion 120 toward proximal end 115 that are perpendicular to the longitudinal axis of cylinder 105, or that are at an angle with respect to the longitudinal axis of cylinder 105, or channels that extend laterally around the circumference of outer surface 130 within distal portion 120). Such embodiments having portions of relatively reduced diameter can allow device 100 to hold a greater amount of hemostatic agent 140 where it will be needed most, i.e., near distal end 125, which can be placed in contact with kidney tissue. The diameter of cylinder 105 can provide pressure along the percutaneous tract while hemostatic material 140 takes effect.

Device 100 also can include barrier 150 over hemostatic material 140. Barrier 150 can be, for example, a thin plastic film, and can be broken and/or removed at the time the percutaneous sheath is removed to allow for precise deployment of hemostatic material 140 along the course of the percutaneous tract. In some embodiments, barrier 150 can be a heat sealed plastic covering that can break away at distal end 125. In some cases, barrier 150 can be scored or perforated at or near distal end 125 to facilitate breakage and removal of barrier 150. The presence of barrier 150 over hemostatic material 140 can prevent early activation or dislodgement of material 140, as most percutaneous tubes are subjected to a constant flow of blood, irrigant (normal saline), or urine during use. Further, exterior surface 130 of cylinder 105, which interfaces with hemostatic material 140, can be negatively charged, sufficiently slick, or coated in such a way that hemostatic material 140 will preferably maintain contact with bodily tissue rather than with device 140 once barrier 150 is broken and/or removed. For example, exterior surface 130 can be coated with TEFLON®. This can facilitate removal of device 100 after a suitable length of time (e.g about 30 seconds to about 5 minutes), without dislodging a newly formed clot.

Device 100 also can have a protrusion (e.g., handle or collar 160) that is connected to barrier 150 and that can be actuated to break or remove barrier 150 from device 100 in order to expose hemostatic material 140. Collar 160 can be located at or near proximal end 115 of cylinder 105. By pulling on collar 160 in a proximal direction, a user can break barrier 150 (e.g., at distal end 125) and then pull barrier 150 proximally over the surface of cylinder 105, exposing hemostatic agent 140 to the surrounding tissue.

Device 100 also can have include one or more radio-opaque markers (e.g., radio-opaque marker 170) so that the position of device 100 can be observed radiographically during deployment. Cylinder 105 of device 100 also can allow for visual confirmation of deployment at the edge of the renal tissue. Marker 170 can be positioned anywhere on device 100, e.g., at or around distal end 125 of cylinder 105 as shown in FIG. 2, or along the surface of distal portion 120. Suitable radio-opaque materials are known in the art, as are methods for depositing radio-opaque markers on medical devices.

Figure 3:
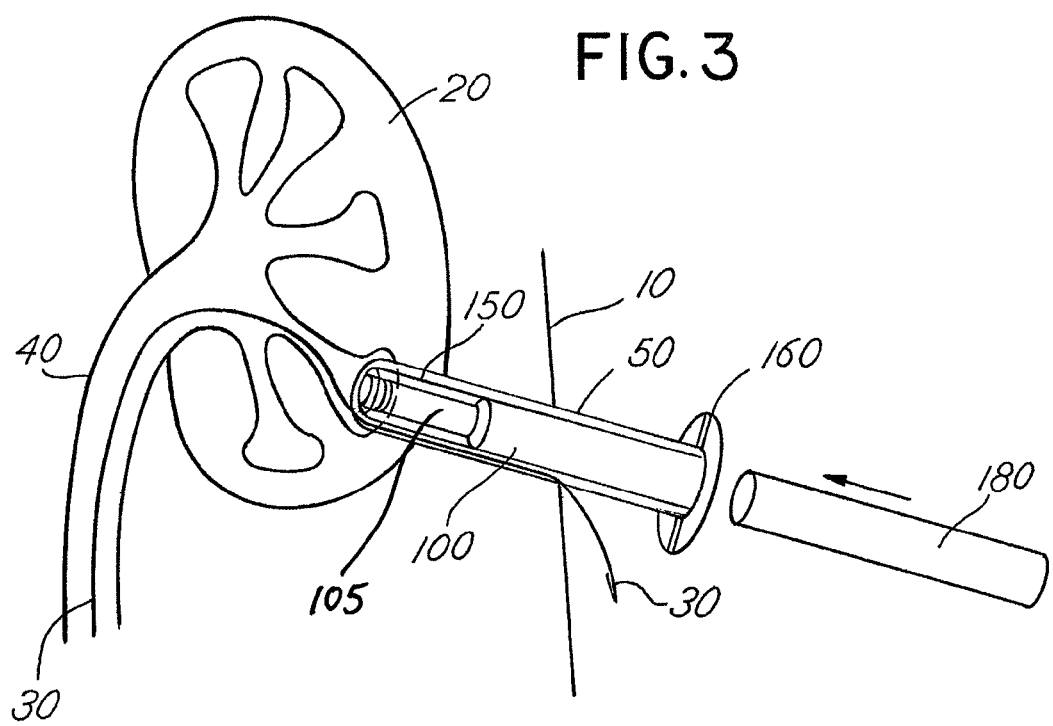
FIG. 3 is a side view of an embodiment of a hemostatic device in use.
Figure 4:
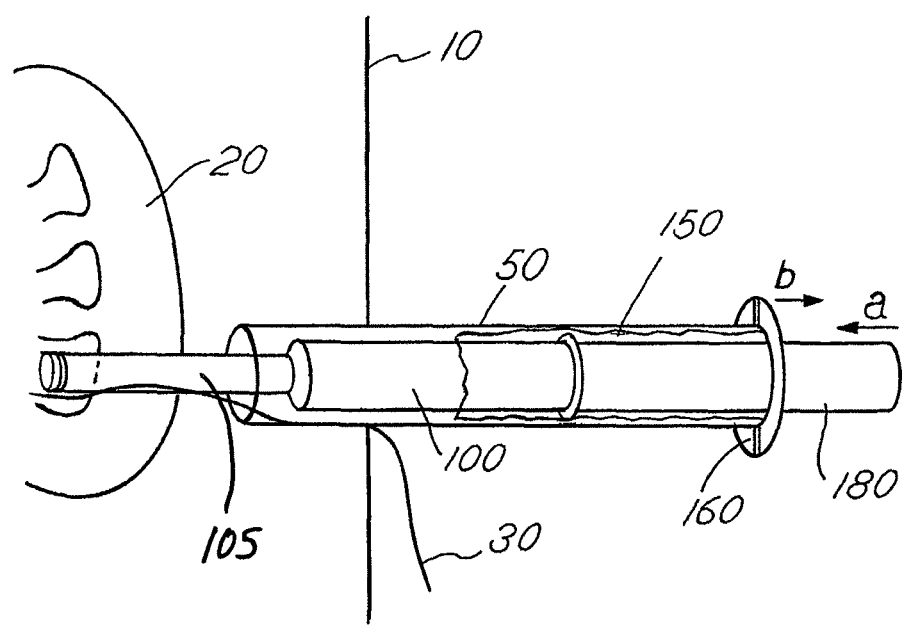
FIG. 4 is a side view of an embodiment of a hemostatic device in use.

FIGS. 3 and 4 depict embodiments of methods for using device 100. Once a medical procedure (e.g., a kidney stone removal or a kidney biopsy) is complete and other medical devices are removed from percutaneous sheath 50, device 100 can be inserted into sheath 50 until distal end 125 reaches kidney 20 (e.g., the distal end of sheath 50 within kidney 20). A user then can insert a driver (e.g., cylindrical driver 180 having distal end 185) into percutaneous sheath 50 (as indicated by the arrow in FIG. 3), advancing driver 180 until distal end 185 contacts proximal end 115 of cylinder 105. In some embodiments, cylinder 105 can have a shelf or protrusion at or adjacent to proximal end 115, on which driver 180 can seat and be used to exert force on cylinder 105 in a distal direction.

The user then can remove percutaneous sheath 50 from the subject by pulling it over driver 180. Simultaneously or subsequently, the user can move handle 160 in a proximal direction, pulling barrier 150 over exterior surface 130 of cylinder 105 and removing barrier 150 from the subject's body while holding cylinder 105 in place. This can be accomplished, for example, by exerting force in a distal direction on driver 180 (arrow "a" in FIG. 4) while exerting force in a proximal direction on handle 160 (arrow "b" in FIG. 4). In some embodiments, the action of removing sheath 50 can also move handle 160 in a proximal direction. In either embodiment, such movement can expose hemostatic material 140 to the subjects kidney and any other tissue surrounding device 100 within the subject's body. It is noted that driver 180 can be hollow such that a lumen extends through its length. Such a hollow driver, in combination with a hollow hemostatic device can allow a user to insert or maintain wires or other instruments into the subject's kidney as needed.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An article comprising:
an elongate member having an exterior surface and an interior lumen through which surgical implements can be placed when said elongate member is placed in a wall of an internal organ;
a hemostatic material in contact with at least a portion of said exterior surface;
a covering that surrounds said hemostatic material and is adapted to move slidably over said elongate member;
said exterior surface of said elongate member having a channel portion that retains said hemostatic material, and said channel portion extending laterally around the outer circumference of said exterior surface and configured to apply pressure along the interior of said wall of said internal organ at the site of hemostatic material retention after said covering is slidably removed;
said channel portion of said elongate member is negatively charged to facilitate contact between said hemostatic material and said bodily tissue of said internal organ when said covering is removed; and
said elongate member configured achieve hemostasis by the simultaneous application of said hemostatic material and said pressure exerted by said exterior surface of said elongate member while said surgical implements remain in said interior lumen for performing surgery on said bodily organ.

2. An article comprising:
an elongate member having an exterior surface and an interior lumen through which surgical implements can be placed when said elongate member is placed in a wall of kidney;
said exterior surface of said elongate member having a distal portion and a proximal portion, said outside diameter of said distal portion being smaller than said outside diameter of said proximal portion to define a channel extending laterally around the outer circumference of said exterior surface;
hemostatic material located only on said distal portion of said elongate member;
a plastic film surrounding said hemostatic material configured to be broken and removed for deployment of said hemostatic material along a course of said percutaneous tract;
at least a portion of said distal portion is negatively charged to facilitate contact between said hemostatic material and said bodily tissue of said internal organ after said plastic film is removed; and
said exterior surface of said elongate member configured to apply pressure along the percutaneous tract of said kidney and retain said hemostatic material at said location of applied pressure to achieve hemostasis after said plastic film is removed, wherein the elongate member achieves hemostasis in said percutaneous tract while surgery is performed on said kidney using said surgical implements placed in said interior lumen.

3. A device for use in percutaneous procedures comprising:
a kit insertable into an interior wall of a kidney;
said kit having an elongate member with an interior lumen through which surgical implements can be placed when said elongate member is placed in said wall of said kidney, a layer of hemostatic material located on said elongate member; a covering over said elongate member and hemostatic material; and
at least one channel on an exterior surface of said elongate member, said channel extending from a distal end of said elongate member toward a proximal end of said elongate member, said channel configured to retain hemostatic material on said elongate member after said covering is removed from said kidney and configured to simultaneously apply hemostatic material to said interior wall along said channel and circumferentially apply pressure to said wall of said kidney to achieve hemostasis at said interior wall while surgery on said kidney is performed via surgical implements contained inside said lumen of said elongate member, and said channel is negatively charged to facilitate contact between said hemostatic material and said bodily tissue of said kidney after said covering is removed.

* * * * *